United States Patent
Schürenberg et al.

(10) Patent No.: US 7,667,196 B2
(45) Date of Patent: Feb. 23, 2010

(54) SAMPLE PREPARATION FOR MASS SPECTROMETRIC IMAGING

(75) Inventors: Martin Schürenberg, Tarmstedt (DE); Christoph Nordmann, Bremen (DE); Mirko Klinski, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 255 days.

(21) Appl. No.: 11/737,380

(22) Filed: Apr. 19, 2007

(65) Prior Publication Data

US 2007/0278400 A1    Dec. 6, 2007

(30) Foreign Application Priority Data

Apr. 27, 2006  (DE) .................. 10 2006 019 530

(51) Int. Cl.
*H01J 49/04* (2006.01)
(52) U.S. Cl. .................................................. 250/288
(58) Field of Classification Search .................. None
See application file for complete search history.

(56) References Cited

U.S. PATENT DOCUMENTS

| | | | |
|---|---|---|---|
| 4,793,339 A | 12/1988 | Matsumoto et al. | |
| 5,382,793 A | 1/1995 | Weinberger et al. | |
| 5,770,272 A | 6/1998 | Biemann et al. | |
| 5,808,300 A | 9/1998 | Caprioli | |
| 6,414,306 B1* | 7/2002 | Mayer-Posner et al. | 250/288 |
| 6,825,463 B2 | 11/2004 | Karger et al. | |
| 6,855,925 B2 | 2/2005 | Ellson et al. | |
| 2002/0094582 A1* | 7/2002 | Williams et al. | 436/180 |
| 2004/0126894 A1 | 7/2004 | Nelson et al. | |
| 2005/0153344 A1* | 7/2005 | Diamond et al. | 435/6 |
| 2005/0156056 A1 | 7/2005 | Larson et al. | |
| 2006/0063145 A1 | 3/2006 | Suckau et al. | |
| 2006/0138319 A1* | 6/2006 | Barnes et al. | 250/288 |
| 2006/0223955 A1* | 10/2006 | Bezuidenhout et al. | 525/453 |

FOREIGN PATENT DOCUMENTS

| | | |
|---|---|---|
| DE | 199 37 438 C2 | 8/1999 |
| DE | 10 2004 037 512.7 | 3/2006 |
| GB | 2425178 A | 10/2006 |
| JP | 10-267 806 A | 10/1998 |
| WO | WO 2005/059552 A1 | 6/2005 |
| WO | WO 2005/101452 A1 | 10/2005 |

OTHER PUBLICATIONS

Luxembourg, et al., "Effect of Local Matrix Crystal Variations in Matrix-Assisted Ionization Techniques for Mass Spectrometry", Anal. Chem., May 15, 2003, pp. 2333-2341, vol. 75, No. 10.
Stoeckli, et al., "Molecular Imaging of Amyloid βPeptides in Mouse Brain Sections Using Mass Spectrometry", Analytical Biochemistry, 2002, pp. 33-39, vol. 311, Elsevier Science.
Aerni, et al., Automated Acoustic Matrix Deposition for MALDI Sample Preparation, Anal. Chem., 2006, 78, 827-834.

* cited by examiner

*Primary Examiner*—Jack I Berman
(74) *Attorney, Agent, or Firm*—Law Offices of Paul e. Kudirka

(57) ABSTRACT

A method for applying MALDI matrix substances to a surface, especially a histologic thin tissue section, for spatially-resolved mass spectrometric measurements of substance distributions in or on the surface uses vibration to nebulize a solution of the matrix substance without the assistance of a gas and deposits the nebulized droplets, preferably cyclically, on the surface.

28 Claims, 1 Drawing Sheet

SAMPLE PREPARATION FOR MASS SPECTROMETRIC IMAGING

BACKGROUND

The invention relates to the application of matrix substances to surfaces for spatially resolved mass spectrometric measurement of substance distributions in or on these surfaces, especially in histologic thin tissue sections, with ionization by matrix-assisted laser desorption.

The invention provides a method of nebulizing a solution of the matrix substance by vibration without the assistance of gas, and depositing the nebulized droplets, preferably cyclically, on the surface being analyzed.

The state of a tissue section in respect of pathologic change, infection, metabolic anomalies, or stress caused by medication, may be visible in the form of changes to the substance composition compared to the normal state of this tissue. The tissue state can thus be identified from concentration patterns of substances. If the concentrations are sufficiently high, then these concentration patterns can be detected mass spectrometrically. The substances here can be peptides or proteins which are under, or over, expressed and hence form an unusual pattern, but they can also represent posttranslational modifications of proteins, their breakdown products (metabolites), or collections of other substances in the tissue.

Mass spectrometry with ionization of the samples by matrix-assisted laser desorption and ionization (MALDI) has been used successfully for several years for the determination of molecular weights, and for identification and structural characterization of the molecules of substances, particularly of proteins and peptides. In such a case, the protein is usually dissolved and mixed with a solution of a matrix substance such as sinapic acid before being applied to the sample support. The solvent then vaporizes and the matrix substance crystallizes; the protein also crystallizes within the matrix crystals in the form of individual molecules which are widely spaced. If the sample obtained in this way is bombarded with short pulses of laser light with sufficient energy, the matrix substance absorbs energy and explosively vaporizes, the proteins being entrained into the surrounding vacuum of the mass spectrometer by the vapor cloud and ionized by protonation. There are several dozen matrix substances which are suitable in principle; half a dozen different matrix substances have become widely used. Different matrix substances have proved to be optimal for different analytical tasks.

The mass spectrometer separates the ions according to their mass-to-charge ratio (m/z, also termed here the "charge-related mass") and measures them as a mass spectrum. The mass spectrum can be used to determine their charge-related mass m/z and hence their physical mass m. Since ionization by matrix-assisted laser desorption provides essentially only singly charged ions, we will refer in the following, for the sake of simplification, only to the "mass determination" and not to the determination of the charge-related mass and, correspondingly, simply to the "mass" m of the ions rather than their m/z ratio.

The mass spectrometric analyses can be carried out on individually obtained, homogeneous biological samples such as tissue homogenates, lyzed bacteria and biological fluids (urine, blood serum, lymph, spinal fluid, tears, sputum), the samples generally being subjected to sufficient fractionation beforehand by chromatographic or electrophoretic techniques. This particularly frees the samples from interfering impurities such as certain buffers, salts or detergents. This removal of interfering impurities of widely varying types is particularly important since they can reduce the ion yield of the MALDI ionization for the analyte substances. The effect of the impurities is not completely understood: it is possible, for example, to observe that simply diluting of the sample, i.e. diluting the impurities as well as the analyte substance in relation to the matrix substance, often brings about a significant improvement of the mass spectrum with respect to the detectability of the analyte substances. The ratio of analyte to impurity remained constant here, indicating that the effect of the impurities is of a higher order than simply linear, and also that there are saturation effects or other suppressive effects for the ionization of the analyte substances. Yet the simple explanation that impurities successfully compete with the analyte substances for the proton sources appears to be incorrect. The presence of detergents, in particular, seems to impede ionization in a general way, without noticeable proportions of ions of these detergents being formed.

The analysis of biological samples thus usually involves very time-consuming sample preparation, particularly if, at the same time, the information concerning the distribution of a protein in different regions of a tissue is to be obtained by measuring individual samples. A method such as "laser capture microdissection" may achieve this but the above-mentioned complex preparation is still necessary, and there is also the difficulty of obtaining sufficient material for this type of analysis.

Imaging mass spectrometry (IMS) makes it unnecessary to go to these lengths. With this method, a thin tissue section having a thickness of between 10 and 20 micrometers is produced, for example using a cryo-microtome, from a frozen piece of tissue taken from an organ of interest, whether human, animal or plant. The thin section is laid on an electrically conductive sample support, for example a conductively coated glass specimen slide. The thin section melts during this process and spreads out smoothly on the sample support. These methods are familiar to the specialist. A layer of a matrix material from a matrix solution is then applied to the dried thin section using a suitable method, which can also involve a reduction in the interfering influence of impurities. After the matrix layer has dried, the specimen slide is introduced directly into the mass spectrometer. There are two different methods for the subsequent mass spectrometric scan: the raster scan method and stigmatic imaging of the ions of a small region.

The raster scan method produces a one- or two-dimensional intensity profile for individual proteins by scanning a thin tissue section with well-focused laser beam pulses in a MALDI mass spectrometer, the proteins being identifiable in the mass spectra obtained for each raster point (U.S. Pat. No. 5,808,300; Caprioli). Each spot is therefore irradiated at least once with a fine-focused pulse of laser light with a diameter of less than 50 micrometers and provides a mass spectrum which can cover a broad range of molecular weights, for example 1 to 30 kilodaltons. Using suitable software, it is then possible to define an ion mass which represents one peptide or one protein, or a narrow mass range around this mass, in the spectra, and to graphically represent its intensity distribution over the surface of the thin tissue section. Using this method it has been possible to correlate the distribution of neuropeptides in the brain of a rat with specific morphological peculiarities, for example, or to portray the distribution of amyloid beta peptides in the brains of Alzheimer animal models. It is possible to represent spatially precisely defined sections of the brain with "Alzheimer plaques" (Stoeckli M., Staab D., Staufenbiel M., Wiederhold K. H., Signor L., Anal Biochem. 2002, 311, 33-39: Molecular imaging of amyloid beta peptides in mouse brain sections using mass spectrometry).

Stigmatic imaging irradiates a defined area of up to 200 by 200 micrometers with the laser pulse. The ions formed over the area are imaged ion-optically spot by spot onto a spatially resolving detector. It has so far been possible to use this method to scan distribution images of these ion masses by careful selection of individual ion masses (S. L. Luxembourg et al., Anal. Chem. 2003; 75, 1333-41); it is to be expected, however, that very rapid cameras will enable complete mass spectra to be scanned for every spot on the area.

In both cases, raster scan and stigmatic imaging, it is necessary, as described above, to coat the surface of the specimen with a matrix material which absorbs laser energy and ionizes analyte molecules. It is not easy to apply the matrix material in this way because (a) a lateral smearing of the analyte substances must be avoided, (b) the analyte molecules must preferably be extracted from the specimen and embedded into the crystals of the matrix material, and (c) a favorable ratio of analyte molecules to impurities must be achieved. The matrix material here is always applied in dissolved form and crystallizes during a drying process. The solvents are usually mixtures of water and organic solvents, for example acetonitrile. Pure water generally cannot dissolve the matrix substances.

Accordingly, the solvent has to extract analyte molecules from the thin section and transport them vertically into the supernatant solution without distributing them laterally in the process. The organic fractions of the solvent play a particularly important role here, even though many analyte molecules can be dissolved in water. The solvent must first penetrate into the thin layer. The solution on the surface then slowly begins to dry, and consequently the matrix materials crystallize out. The drying process causes the solvents to be drawn out of the thin layer again, a process which probably involves capillary forces and, primarily, osmosis. Analyte molecules are also transported into the drying supernatant solution. It is favorable for the MALDI process if the analyte molecules to be ionized are embedded into the crystals of the matrix material; at the least, the analyte molecules must be in close contact with the matrix materials, for example by being deposited on the grain boundaries of the crystals.

The matrix materials can, for example, be applied by pneumatically spraying a matrix solution in the form of a fine spray droplets onto the thin section as described in U.S. Pat. No. 5,770,272 (Biemann et al.). As described above, the solution must stay on the thin section for a certain length of time before the matrix material crystallizes out in order that the solvent can penetrate into the thin section specimen and the analyte molecules, i.e. mainly the proteins and peptides, can be extracted from the thin section and hence have the chance of being embedded into the crystals. Pneumatic spraying, however, has the disadvantage that it is not possible to prevent the gas stream from macroscopically moving the spray droplets, which have very low viscosity, over the thin section. This reduces the lateral accuracy of the mass spectrometric analysis through lateral smearing.

Pneumatic spraying can also be used for other types of surface whose substance distributions are to be measured. It has been used in this way for thin-layer chromatography (DE 199 37 438 C2; Maier-Posner and Franzen; corresponding to U.S. Pat. No. 6,414,306 B1).

The development of pneumatic spraying for thin section specimens has shown that it is favorable to only spray on a very small amount of matrix solution at a time and to repeat this spraying very frequently. Large quantities of individual spray droplets are applied in each round of spraying but not so many that the spray droplets on the surface can merge to form a film of liquid. Between the individual spraying rounds, the sprayed-on droplets should be able to slowly dry, in around 30 seconds. Thus, for example, the spray is applied for several seconds, followed by a drying period of approx. 30 seconds. A carefully metered gas stream is used for the drying. The spraying processes here typically have to be repeated between a hundred and two hundred times in order to obtain mass spectra which can be readily analyzed. If there are too few spraying cycles, the analyte signals in the mass spectra are noticeably weaker or not present at all.

This method can, of course, be automated, but it is usually carried out manually, generally with so-called airbrush pistols, because of a lack of commercially available instruments. This requires a lot of patience and skill because it takes hours. Even if the user constructs an automatic device himself, the reproducibility is not satisfactory. The gas stream used with pneumatic spraying transports the droplets over macroscopic distances, i.e. up to several millimeters. If the spraying is too "wet", the droplets merge to form a liquid film in which the gas stream causes the formation of an outward radial flow which delocalizes the analyte molecules. The other extreme is spraying which is too "dry", where the solvent has already completely vaporized in the flight phase and the matrix impinges on the thin section as a dry crystal shower. In this case, no analyte molecules can be embedded into the matrix. It is very hard to find a happy medium between these two extremes. The two-dimensional spreading of the droplets which are blown onto the surface limits the lateral resolution to around 200 micrometers. The gas stream used for the pneumatic spraying serves to dry the sprayed droplets initially, the organic solvent being the first to escape from the droplets. A larger proportion of water remains, but this is not so good for extracting the proteins from the surface of the thin section. It is therefore necessary to use a large proportion of organic solvent and a low concentration of the matrix material, but this lengthens the process.

The disadvantages of pneumatic spraying have led to the development of another method which does not have this disadvantage of spray droplets in the gas stream: the application of individual droplets by so-called nanospotters. Nanospotting can be done with either piezoelectric or solenoid spotters. Droplets with typical volumes of between 100 picoliters and 10 nanoliters can be shot onto the thin section without contact between nanospotter and section. It has been found that droplets between 10 and 30 micrometers in diameter are most suitable. If the droplets are much smaller, they dry too quickly for the analyte molecules to be efficiently extracted from the tissue. Here too, the liquid must be allowed to act on the thin section for around 30 seconds before the droplets dry, causing the matrix materials to crystallize out completely.

The positioning accuracy of the nanospotter makes it possible to apply the droplets with a lateral repeat precision of the spotter position of a few micrometers, although, depending on the immediate surroundings of the thin section, the droplets are laterally deflected by several micrometers in a statistically distributed direction. It is possible to spot the droplets precisely one on top of the other, but their position does not necessarily correspond to the selected grid. There is a commercial nanospotter on the market for which a method has been developed for applying the droplets in a very precise positioning grid with a separation of 150 to 200 micrometers in each direction. A sufficiently large separation is selected so that the droplets do not run into each other. The droplet size of around 20 micrometers diameter (around ten picograms)

results in application spots around 100 micrometers in diameter. Each individual spot is applied again at intervals of around 30 seconds; this application is repeated a few hundred times for each spot. This method of applying the matrix substance also takes several hours.

The mass spectra obtained with this method of nanospotting are high quality but the method is not cheap because a very expensive instrument is used. The method produces much better mass spectra of the analyte substances than is possible with the pneumatic spray method, and a slightly better lateral resolution of around 100 to 150 micrometers, depending on the grid of the spotting. The mass spectrometric measurement requires image recognition to position each individual spot with matrix crystals, however. Since the MALDI process of ionizing analyte molecules can be readily carried out with laser focus points of around 30 micrometers in diameter, this method of nanospotting is not optimally adapted to the achievable lateral resolution of MALDI mass spectrometry.

SUMMARY

The invention provides a method for applying a layer of matrix crystals to the surface of a target on which the spatial distribution of analyte molecules is to be measured mass spectrometrically with ionization by matrix-assisted laser desorption. The method comprises the following steps:
(a) providing a solution of the matrix substance,
(b) providing a body in contact with the matrix solution and in contact with a vibrator,
(c) nebulizing the matrix solution by vibrating the body to form a cloud of nebulized droplets, and
(d) depositing the nebulized droplets on the surface of the target.

If the density of the droplets which deposit on the target is sufficiently small, and if the deposited droplets dry quickly enough, then the nebulization can be carried out continuously until sufficient matrix material has been applied. It has proved to be favorable, however, to nebulize the matrix solution only in short bursts interspersed with short intervals to allow at least partial drying of the nebulized droplets deposited. The bursts of nebulization can be between 0.5 and 5 seconds; one to two seconds is best. The drying intervals can be between 10 and 60 seconds, the optimum length being 20 to 40 seconds.

The term "target" here can refer to thin section specimens and also to other specimens which have analyte substances in non-homogeneous distribution either on the surface or in the material directly below the surface, the spatial distributions of which are to be determined by mass spectrometry. Such a target can be a chromatographic thin layer, a gel electrophoretic membrane or a blot membrane, for example. A blot membrane can, for instance, be a copy with analyte substances from a thin section specimen. The mass spectrometric analysis can just involve the determination of the molecular weight, but it can also include a more detailed identification of the analyte substance.

"Nebulization by vibrating a body" or, in short, "vibrating nebulization" means that the matrix solution is nebulized by a vibrating body which shakes matrix solution droplets off its surface, in particular without the aid of a pneumatic nebulization. Vibrating nebulization has the major advantage that the nebulized droplets do not have to fly in a pneumatically produced gas stream and hence are not subjected to forced drying during the flight.

Such vibrating nebulization can easily be brought about by a thin, elastic membrane which is excited to vibrate in one of its overtones. It is preferable to use a metal membrane around 0.1 to 0.2 millimeters thick. If the end of this membrane is immersed in a "footbath" of matrix solution, the matrix solution is automatically drawn up the vibrating membrane in fractions of a second and nebulized. The membrane can also be perforated with a number of thin holes, and the solution is fed to the backside of the membrane, penetrating the perforations. The membrane can be excited by a vibrator, for instance by a piezoelectric crystal, to which the membrane is affixed with adhesive; the most favorable frequencies are in the range between approx. 30 and 200 kilohertz, for example around 120 to 140 kilohertz for a metal membrane 20 millimeters wide, 40 millimeters long and 0.2 millimeters thick. The aim is to find a resonance of an overtone and, for optimum nebulization, to maintain this resonance with a precision of roughly 0.5 kilohertz.

The nebulized droplets are shaken off by the vibration antinodes of the membrane; they have diameters of around 10 to 30 micrometers. Larger droplets are also formed, probably by the merging of smaller droplets. The higher sinking velocity of the heavier droplets allows them to be separated out so that they do not reach the surface of the target. The cloud of nebulized droplets expands of its own accord because a minor vaporization of the nebulized droplets means that the gas volume of the cloud expands continuously until the vapor pressure of the droplets reduced by cooling equals the gas pressure in the cloud. This self-sustained growth of the cloud of nebulized droplets is a further important advantage of the method according to the invention.

The term "depositing the nebulized droplets" should be taken here to mean that the nebulized droplets either deposit of their own accord from the cloud onto the surface of the target, or that the nebulized droplets are actively guided to the target. The nebulized droplets can deposit unaided onto a horizontal target by the force of gravity, or onto a suspended target by lifting forces within the cloud of nebulized droplets (if the solvent vapors are specifically lighter than the ambient gas). The active guidance can be brought about by a light gas stream or, after electrical charging, by an electric field. The nebulized droplets can be electrically charged by shaking them off in an electric field, or by feeding in charged particles, for example beta rays. Charged nebulized droplets have the further advantage that they do not have a tendency to merge together and form larger droplets. Mixtures of active guidance of the nebulized droplets and automatic deposition are also possible.

The "at least partial drying" in the intervals between the bursts of nebulization means waiting until the droplets have dried to the point that crystals clearly have begun to form, although it is quite possible that some liquid remains between the crystals or in the target material. It is expedient, and has proved to be particularly effective, to have longer breaks of a few minutes after several cycles of nebulization, deposition and partial drying so as to allow complete drying. Both for the "at least partial drying" and for the complete drying, a gentle, dried and filtered gas stream can be fed through the chamber which encloses the nebulizer and the device for holding the target.

For thin section specimens, the cycles of nebulization, deposition, and drying must be repeated very frequently overall, generally at least a hundred times, preferably around two hundred times, in order to obtain analyte ions from laser shots that can be readily measured with a mass spectrometer. It appears that there is a coating threshold for the mass spectrometric measurability of the analyte substances. Usable mass spectra with analyte substance signals that can be readily analyzed are only obtained when the threshold is exceeded. A good coating of fine matrix crystals looks like a fine layer of hoarfrost; the differences in the tissues of the thin section can only be seen by means of the profile, and no longer by differences in color. It is not yet known why such a thick coating is required for good mass spectrometric results. It can be assumed, however, that cleaning processes occur here. For other types of targets, for example blot membranes, which can be readily washed, the number of coating cycles does not have to be so high.

A further particular advantage of this method is the fact that the statistical spatial distribution of the applied droplets gradually produces complete coverage of the target. The gentle deposition also means that the droplets do not spread out very much: the coated spot of a deposited drop on a thin section specimen some 10 micrometers thick has a diameter of around 50 micrometers. The lateral resolution is also around 50 micrometers and is thus much better than with the methods according to the prior art.

DETAILED DESCRIPTION

Figure 1:
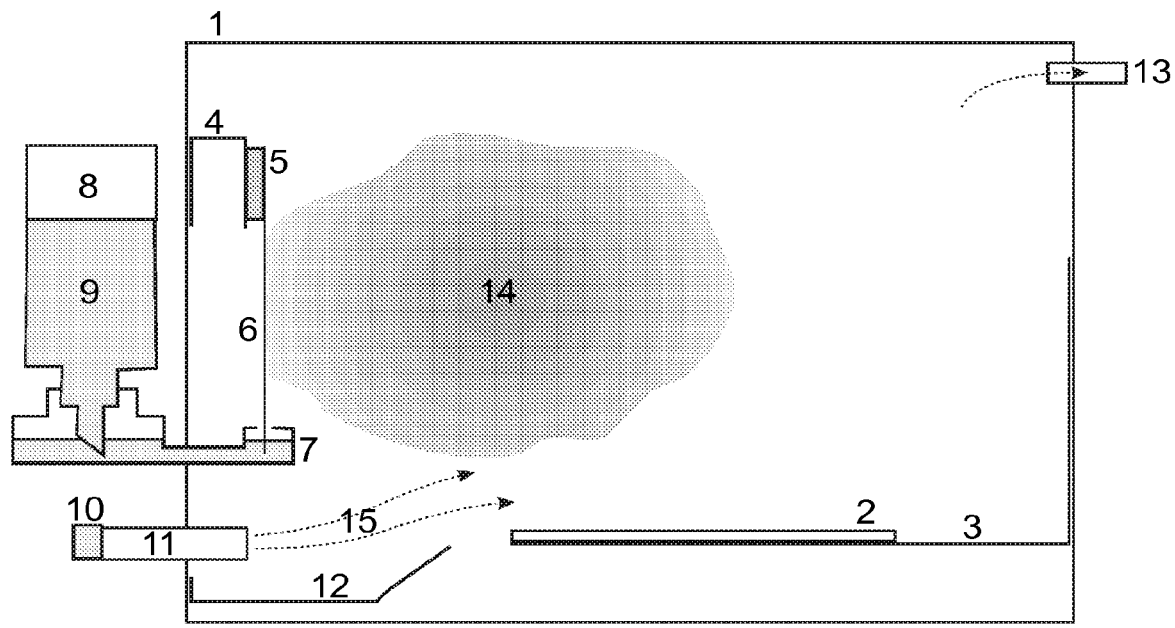
FIG. 1 shows how the nebulization device is accommodated in the chamber (1) in addition to the target (2) on its holding device (3). The nebulization device comprises a fastening device (4), the piezoelectric crystal (5) as the vibrator, and the vibrating membrane (6). The end of the vibrating membrane (6) is immersed in the footbath (7) containing matrix solution, whose level is kept constant by the supply bottle (8) containing matrix solution (9). Vibration of the membrane (6) produces the cloud of mist (14), which expands of its own accord to cover the target (2) and whose droplets deposit onto the target (2). The cloud of mist can also be guided by a weak air stream (15) if necessary. The air stream (15) is formed by gentle suction at the nozzle (13), which draws air through the superfine filter (10) and the channel (11) into the chamber, where the deflector plate (12) guides it to the target (2).

While the invention has been shown and described with reference to a number of embodiments thereof, it will be recognized by those skilled in the art that various changes in form and detail may be made herein without departing from the spirit and scope of the invention as defined by the appended claims.

One preferred embodiment begins with the production of a thin tissue section, preferably from a frozen piece of tissue, using a microtome. The thin tissue section is applied to a suitable support. This support can be a glass specimen slide, for example, whose surface is given a transparent but electrically conductive surface coating for subsequent use in the mass spectrometer. The specialist is familiar with such conductive layers. Other supports, for example metal supports or supports made of electrically conductive plastic, can also be used, however. The frozen thin tissue section melts at room temperature and immediately spreads out thinly on the support and adheres to the support. The thin-layer specimen still adheres firmly to the support even after a drying cycle. The thin tissue section can be stained in the usual way, although care has to be taken to use a stain which does not interfere with a subsequent mass spectrometric analysis of the tissue constituents. Fluorescent stains can also be used if they do not restrict the mass spectrometric analysis. With stains which interfere with the mass spectrometric analyses, only every second section is stained and only the unstained sections are analyzed mass spectrometrically.

After this, a microscopic image is taken of the thin tissue section, either with transmitted or reflected light, and this optical image is later used to lay under the result images. Before the optical image is taken, markings which are recognizable both optically and, if possible, mass spectrometrically can preferably be applied to the support to facilitate subsequent adjustment so as to obtain a true position. Many mass spectrometers are equipped with a viewing unit for the samples which can likewise be used for the true-to-position adjustment.

The thin tissue section on the support (2), referred to below as the "target", is then put into a chamber (1) which also contains the nebulizer. One option is to fix the target (2) to a device (3) which moves the target (2) under the nebulization cloud (14) so as to form a uniform coating of nebulized droplets. Care must be taken that the coating is not so dense that the positional accuracy of the samples is adversely affected by the merging of the deposited droplets. If the nebulization produces a very thin mist, then the nebulization can be continuous. If the nebulization is dense, as is usually the case with the above-described nebulizer, it is generally sufficient to have a few seconds of vibration to generate a cloud of mist with the correct density, but then drying intervals have to be interspersed.

The target (2) does not have to be moved, however. It is possible to achieve very good, uniform coatings without such motion even if the droplet deposition from the cloud of mist (14) only occurs by gravitation, i.e. by the droplets sinking of their own accord under gravity. Coating with nebulized droplets using lifting processes within the cloud of mist can also produce a correct and uniform coating density without moving the target. Other methods of guiding the droplets of the cloud of mist to the target are reported below.

The vibrating device of the nebulizer is also very simple. It consists of a vibrator, here a piezoelectric crystal (5) which is held securely in the chamber (1) by a fastening device (4) and which can be supplied with an RF alternating voltage via voltage feeders. A metal membrane (6) is fixed on the piezoelectric crystal (5), the simplest way being to attach it with an adhesive which is resistant to the solvents used. The metal membrane (6) can be around 20 by 40 by 0.2 millimeters in size. Membranes made of other materials and other sizes can also be used, of course, but they also have to be resistant to the solvents. Metal membranes have so far proved to be the best.

The frequency of the RF voltage across the piezoelectric crystal (5) is selected to coincide with an overtone of the vibrations of the metal membrane (6) in resonance. This creates a pattern of nodal points and vibration antinodes on the membrane. For a metal membrane with the given dimensions, a favorable frequency is roughly between 120 and 140 kilohertz, and definitely in the range roughly between 30 and 200 kilohertz. The frequency should be maintained to within 0.5 kilohertz in order to remain in resonance.

The bottom one or two millimeters of the metal membrane (6) may be immersed in a footbath (7) of matrix solution. The footbath (7) operates like a bird waterer in that it has a supply bottle (8) with matrix solution (9) to keep the level constant. As soon as the metal membrane (6) is set in vibration, the matrix solution from the footbath (7) creeps up the metal membrane (6) to be shaken off at the vibration antinodes in the form of small nebulized droplets. At the stated frequency, a cloud of mist (14) forms, in which around 90 percent of the nebulized droplets have a diameter of between 10 and 30 micrometers. A number of larger droplets are also formed, however, probably by the merging of smaller droplets in the cloud of mist (14). These larger droplets sink much quicker because of the force of gravity and can thus be eliminated before they reach the target (2).

When the vibration is switched on, a cloud of mist (14) with droplets of the matrix solution is created almost immediately. Vibration of one to two seconds produces a cloud (14) several centimeters in diameter. The cloud (14) spreads out of its own accord in the chamber (1), also extending over the target (2) and beyond. As this happens, gravity causes the droplets to slowly sink and they can deposit on the target (2).

On thin section specimens, the individual droplets which deposit on the target (2) flow apart to form moisture spots some 50 micrometers in diameter. They are statistically distributed over the surface. The number of droplets deposited from a cloud (14) created by a vibration of one to two seconds is not high enough to produce a noticeably strong overlapping of moisture spots: the droplets therefore mostly remain separate from each other. The process of nebulization fills the space above the target (2) with solvent vapor. This has the desirable effect of hindering immediate drying of the moisture spots. Drying only proceeds very slowly. The solvent has time to penetrate into the target (2), cause the target material to swell and to liberate analyte molecules.

The drying increases the concentration of the matrix material in the supernatant liquid: the matrix material starts to separate out of the liquid as small individual crystals. This drying process now also retrieves liquid from the target, mainly by osmosis, but also partly by the capillary effect of the spaces between the small matrix crystals. This process also transports the detached analyte molecules. These can be embedded into the small crystals and also deposited in grain boundaries.

If this process of nebulization, droplet deposition and drying is repeated some ten to twenty times, then the target is completely covered with small matrix crystals. The resultant overlapping of new droplets onto old spots which are already dry does not seem to interfere with the lateral resolution to any great degree. If the target is a thin section specimen and if, after only twenty coating cycles, the target (2) is subjected to a mass spectrometric analysis with ionization by means of matrix-assisted laser desorption (MALDI), then the analyte molecules remain invisible in the mass spectrum.

One can only speculate on the reason for this failure. It is possible that the solvent causes not only the analyte molecules to become detached but also many other substances of the thin section specimens. The thin section contains salts and many other substances which are found in the tissue, including many substances which interfere with the MALDI ionization process. It is presumed that, like the analyte molecules, these substances are also transported into the crystal layer and deposited there.

A satisfying result is only achieved when the process of nebulization, droplet deposition and drying has been repeated at least a hundred times, preferably even two hundred. There is then a visible, white layer of small matrix crystals on the thin-layer specimen. It resembles a snow-covered landscape: everything is under a white blanket. It is now possible to obtain very good mass spectra of the analyte substances, i.e. of the proteins and peptides from the thin section specimen, although why this should be so remains a mystery. One explanation could be that both analyte substances and impurities have been diluted, or that these substances have been separated from each other by recrystallization effects or by a different migration rate in the layer of matrix crystals. But the effect itself is not new: it also occurs with the prior methods of coating with matrix material.

The droplet deposition from the cloud of mist (14) can also be actively assisted by various measures, for example in order to uniformly cover larger target areas. It is possible, for example, to electrically charge the droplets by shaking them off in an electric field, for instance by having a DC voltage between target (2) and vibrating metal membrane (6), and to then guide them in the electric field. The droplets can also be charged by means of ionizing radiation, for example by a beta emitter. Charging the droplets is also favorable in another respect: it largely prevents smaller droplets from merging to form larger droplets.

A very simple way of guiding the cloud of mist is to use a weak gas stream (15) which is guided by small deflector plates (12). This is achieved, for example, by mounting an aperture (11) below the vibrator so that a weak current of air which has been thoroughly cleaned of dust in a superfine filter (10) can be drawn into the chamber through this aperture (11). The air can be drawn in through a nozzle (13) which is mounted in another part of the chamber (1), for example. The air stream (15) can be deflected by the deflector plates (12) in such a way that it guides the cloud of mist (14) to the target (2). This air stream (15) can also be used particularly to control the drying process.

It has proved to be particularly favorable to interrupt the coating process for a time after five to twenty cycles of nebulization, droplet deposition and partial drying to allow the coated target (2) to dry thoroughly. A stronger air stream (15) can also be switched on to do this. The break can last for several minutes.

It always takes a very long time to coat thin section specimens. If a cycle of nebulizing, droplet deposition and drying takes only 30 seconds, and if there are only two minutes of powerful drying every ten cycles, then two hundred cycles take around 2.5 hours. It is therefore expedient to automate the process. This can be done with a simple electronic system which controls the vibration and the air extraction, or with a computer-controlled system with a program whose parameters can be optimally adjusted to the respective conditions.

In the long period until the support is completely coated, changes can occur in the coating chamber which interfere with the optimum coating process. The mixture of the solvent in the footbath (7) can change, for example. This mixture usually consists of an organic fraction of solvent, for example acetonitrile or methanol, and water. The organic solvent vaporizes more rapidly than the water, thus increasing the proportion of water and increasing the tendency of the matrix material to crystallize out. The matrix material can quite easily already crystallize out on the vibrating membrane (6), whereby the resonant frequency changes. This can be counteracted if, from time to time, for example during the drying breaks, a small programmed amount of pure solvent is added to the solution in the footbath (7). It can be quite expedient to use this addition of solvent to spray the vibrating membrane (6) to eliminate any crystals which form on it. A sprayer (not shown here) can be mounted in the chamber (1) for this purpose.

Figure 2:
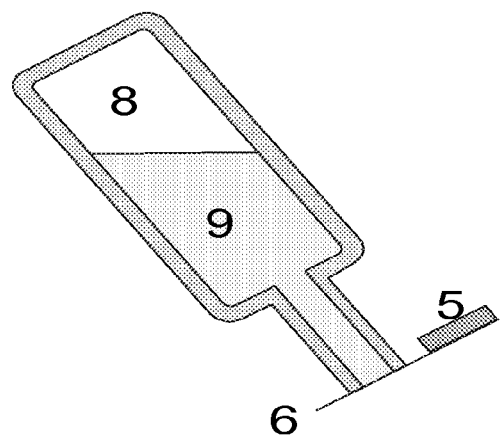
FIG. 2 exhibits a bottle (8), filled with matrix solution (9), held overhead and closed softly in direct contact with a perforated metal vibrating membrane (6) fastened to a piezoelectric crystal (5).

The matrix solution (9) from a supply bottle (8) can also be fed to the vibrating membrane (6) in quite different ways than via the footbath (7). For example, the vibrating membrane (6) can be designed with minute holes to make it porous, and the matrix solution (9) can be fed to the membrane (6) from the rear via a sponge-like material in direct contact. Vibrators of this type were previously used as inhalers. It is also possible to use the perforated vibrating membrane (6) to softly close a bottle (9) with matrix solution (8) by direct contact, as shown in FIG. 2. The slight under-pressure which forms in the bottle (9) after a small amount of solution (8) has flown out is sufficient to hold the perforated membrane (6) in position, and vibrating the perforated membrane (6) by a piezoelectric crystal (5) forms the cloud of droplets. This arrangement has the advantage that any preferred evaporation of organic solvents does almost not occur. The matrix solution does not change its concentration.

The choice of matrix substance can greatly influence which biomolecules, as analyte molecules, lead to signals in the spectra. Proteins, for example, are prepared for the MALDI analysis with 2.5 dihydroxybenzoic acid (DHB) or sinapic acid (SA), peptides with α-cyano-4-hydroxycinnamic acid (CCA), nucleic acids with 3-hydroxypicolinic acid (3-HPA) and saccharide-carrying structures with DHB or with trihydroxyacetophenone.

In another embodiment, the spatially resolved mass spectrometry can be carried out on a copy rather than on the original tissue section. For example, the moist thin tissue section can be brought into contact with a blot membrane either before or after the microscopic image acquisition. Blot membranes are familiar from two-dimensional gel electrophoresis; they can affinitively bind proteins and peptides in a particular way so they are stationary. The substances can be transferred onto the blot membrane by simple diffusion and also by electrophoresis. Dinitrocellulosis membranes are particularly favorable for use as blot membranes for mass spectrometric analyses. For such an analysis, these blot membranes are then used instead of the thin tissue sections and are coated with layers of matrix using the coating method according to the invention. Using blot membranes does have advantages: since the analyte substances are held relatively firmly in the blot membrane, they can be washed in suitable liquids and thus freed from a large proportion of the impurities. The coating process can then involve significantly fewer cycles and still provide very good mass spectra of the analyte substances.

Instead of a blot membrane, a surface which is densely coated with antibody molecules for selected proteins or peptides can be used as the copy medium. This makes it possible to extract various mutants, modification forms and also breakdown forms of a single protein from the tissue and to analyze them with spatial resolution, even if the protein is only present in the tissue at a very low concentration. The ratio of the mutants, modification forms and breakdown forms to each other can also be measured here. It is interesting and extremely informative, for example, to see how a protein primarily occurs singly phosphorylized at some sites while at other sites in the tissue it is triply phosphorylized. The surface of the copy medium can also be coated with several antibodies so that several proteins can be fished simultaneously. The fishing here must not, however, be carried out to saturation if the ratio of the proteins to each other is to be maintained.

Chromatographic thin layers (TLC) are another type of target. Here too, the distributions of the analyte substances are measured. In the prior art, the matrix layer was applied by pneumatic spraying methods.

The targets, i.e. either the prepared thin tissue sections, prepared copies or chromatographic thin layers, are coated with matrix layers before being introduced into the mass spectrometer. The mass spectrometric spectrum acquisitions are then carried out using either the raster scan method with a finely focused pulsed beam of laser light or the stigmatic imaging of the ions generated over a large area.

The raster scan consists of a spot-by-spot recording of the mass spectra. In each spot of the target, the finely focused laser beam delivers the analyte ions for a spectrum acquisition, or preferably for many spectrum acquisitions. The mass spectra from a single spot are added together in order to achieve a higher dynamic range of measurement and also to improve the statistics of the mass signals. The diameters of the "spots" correspond roughly to the diameter of the laser focus, or to be more precise, to the diameter of the laser beam on the sample, which can be set by focusing. For the purposes of the raster scan it is usually possible to set diameters of around 20 to 50 micrometers. The sum spectra are stored for every spot of the raster scan. For a tissue area of one square millimeter, there can thus be 400 to 2,500 mass spectra, although there will usually not be more than 400 spectra.

The raster is generally made of measuring spots arranged in a square, a parallelogram or a honeycomb shape, but it can, of course, also dispense with this type of pattern and instead follow a special morphology of the target, as would be helpful, for example, in the case of an axon of a ganglion several millimeters long. The only thing which matters here is that the distances between the measuring spots are adjusted to match the size of the area irradiated by the laser.

Ions generated by MALDI can be analyzed with mass spectrometers using a wide variety of mass analyzers. Time-of-flight mass spectrometers (TOF-MS) with or without ion reflectors are the usual method. Time-of-flight mass spectrometers with orthogonal ion injection can also be used, however. Ion traps and Fourier transform ion cyclotron resonance (FT-ICR) are also increasingly being used.

The stigmatic imaging generates around 10 to 20 spatially resolved mass signals from an irradiated area around 200 micrometers in diameter on a spatially resolving detector. This is done using time-of-flight mass spectrometers with special ion focusing systems for stigmatic imaging. The current art consists in only scanning the ion current signal for each laser pulse over a narrow mass range, and masking out the remaining mass ranges, since the time resolution of the detectors permits no other way of measuring. The measurements must be repeated each time for other mass ranges. The choice of the mass ranges is matched to those masses which have proved to be significant in previous analyses. It is to be expected, however, that in the future there will be cameras with better time resolution. It will then be possible to acquire the complete mass spectra for a multitude of spots; but the question of the mass resolving power is as yet unanswered. The spatial resolution of this method promises to be better than that of the raster scan. Larger areas are scanned one after the other like a mosaic.

After the measurements, complete or mass-selected mass spectra are then available for each tissue spot. Suitable imaging methods enable specific analyte substances to be selected by virtue of their ion masses and portrayed as a two-dimensional image. It is also possible to portray several analyte substances in several colors at the same time. The image can be underlaid with a microscopic image of the thin tissue section.

The mass spectrometric data can also be used to calculate special "characteristics that distinguish between different tissue states" for every spot. This involves the use of detailed computational methods comprising algorithms and parameter sets obtained in the form of "biomarkers" in pre-analyses of cohorts of samples. These tissue state characteristics are then displayed graphically—preferably superimposed in color on the representation of the microscopic image in gray color. Methods such as this are described in the patent application publication DE 10 2004 037 512.7 (corresponding to publications GB 2 418 773 A or US-2006-006315-A1)

In further embodiments, three-dimensional images of a tissue, for example through several layers of thin tissue sections, can also be acquired.

What is claimed is:

1. A method for applying a layer of crystals of a matrix substance to the surface of a target in which a spatial distribution of analyte molecules in or on an area of the target surface is to be measured mass spectrometrically with ionization by matrix-assisted laser desorption, comprising:
   (a) providing a solution of the matrix substance,
   (b) positioning a body in contact with the solution and in contact with a vibrator,
   (c) nebulizing the solution by vibrating the body to form a cloud of nebulized droplets, wherein the cloud contains a plurality of droplets, and
   (d) positioning the target area and the cloud of droplets relative to each other so that the nebulized droplets in the cloud are deposited over substantially the entire target area.

2. The method of claim 1, wherein step (c) is repeated in bursts of around 0.5 to 5 seconds, interspersed with drying intervals of 10 to 60 seconds to allow the deposited nebulized droplets to at least partially dry.

3. The method of claim 2, wherein the bursts of nebulization last around 1 to 2 seconds and the drying intervals of the deposited nebulized droplets last around 20 to 40 seconds.

4. The method of claim 2, wherein the bursts of nebulization and the drying intervals of the deposited nebulized droplets are repeated at least 100 times.

5. The method of claim 1, wherein step (c) comprises adjusting vibration of the body to generate predominantly nebulized droplets with diameters of between 10 to 30 micrometers.

6. The method of claim 1, wherein the body is a membrane and wherein step (c) comprises vibrating the membrane with oscillation frequencies in the range between 30 and 200 kilohertz.

7. The method of claim 6, wherein step (c) further comprises vibrating the membrane with a piezoelectric crystal serving as the vibrator.

8. The method of claim 7, wherein the membrane is perforated, and the matrix solution penetrates the perforations.

9. The method of claim 1, wherein step (d) comprises positioning the target so that nebulized droplets are deposited on the target under the influence of gravity.

10. The method of claim 1, wherein step (d) comprises electrically charging nebulized droplets and electrically guiding charged nebulized droplets to the target.

11. The method of claim 1, wherein step (d) comprises guiding nebulized droplets with assistance of a gas stream.

12. The method of claim 1, further comprising the step of (e) drying of deposited nebulized droplets with assistance of a gas stream.

13. The method of claim 12, wherein steps (c) and (d) are controlled by one of electronics and a computer.

14. The method of claim 1, wherein the surface of the target is the surface of a histologic thin section.

15. The method of claim 1, wherein the surface of the target is the surface of a thin-layer chromatographic coating.

16. The method of claim 1 wherein step (c) comprises forming a nebulized droplet cloud of having a size that is comparable to the target area so that, in step (d), nebulized droplets in the cloud are deposited over substantially the entire target area without moving the target area relative to the body.

17. The method of claim 1 wherein step (c) comprises forming a nebulized cloud that expands in a direction parallel to the target area so that the nebulized droplets in the cloud are deposited on the target area under the influence of gravity.

18. Apparatus for applying a layer of crystals of a matrix substance to the surface of a target in which a spatial distribution of analyte molecules in or on an area of the target surface is to be measured mass spectrometrically with ionization by matrix-assisted laser desorption, comprising:
   a membrane in contact with a solution containing the matrix substance;
   a vibrator that vibrates the membrane to form a cloud of nebulized droplets, wherein the cloud contains a plurality of droplets, and
   means for positioning the target area and the cloud of droplets relative to each other so that the nebulized droplets in the cloud are deposited over substantially the entire target area.

19. The apparatus of claim 18, wherein means for positioning comprises means for positioning the target so that nebulized droplets are deposited on the target under the influence of gravity.

20. The apparatus of claim 18, wherein the means for positioning comprises means for electrically charging nebulized droplets and means for electrically guiding charged nebulized droplets to the target.

21. The apparatus of claim 18, wherein the means for positioning comprises means for guiding nebulized droplets with assistance of a gas stream.

22. The apparatus of claim 18 wherein the membrane that forms the nebulized droplet cloud has a size that is comparable to the target area so that nebulized droplets in the cloud are deposited over substantially the entire target area without moving the target area relative to the membrane.

23. The apparatus of claim 18 wherein the membrane is positioned at a non-zero angle with respect to the target area.

24. The apparatus of claim 23 wherein the angle is 90°.

25. The apparatus of claim 18 wherein the membrane is perforated and the matrix solution penetrates the perforations.

26. The apparatus of claim 18 wherein only one edge of the membrane is in contact with the matrix solution and the matrix solution is drawn over the membrane due to the vibration.

27. The apparatus of claim 18 wherein the membrane is extends in a vertical direction.

28. The apparatus of claim 27 wherein only the lower edge of the membrane contacts the matrix solution.

* * * * *